US010151717B2

United States Patent
Lees et al.

(10) Patent No.: US 10,151,717 B2
(45) Date of Patent: Dec. 11, 2018

(54) LUBRICANT ANALYSIS USING X-RAY FLUORESCENCE

(71) Applicant: The University of Sussex, Brighton (GB)

(72) Inventors: John Lees, Leicester (GB); David Bassford, Leicester (GB); Anna Barnett, Sussex (GB)

(73) Assignee: The University of Sussex, Brighton (GB)

( * ) Notice: Subject to any disclaimer, the term of this patent is extended or adjusted under 35 U.S.C. 154(b) by 50 days.

(21) Appl. No.: 14/912,591

(22) PCT Filed: Aug. 20, 2014

(86) PCT No.: PCT/GB2014/052552
§ 371 (c)(1),
(2) Date: Feb. 17, 2016

(87) PCT Pub. No.: WO2015/025160
PCT Pub. Date: Feb. 26, 2015

(65) Prior Publication Data
US 2016/0202194 A1    Jul. 14, 2016

(30) Foreign Application Priority Data
Aug. 22, 2013  (GB) .................................. 1315024.8

(51) Int. Cl.
*G01N 31/22*    (2006.01)
*G01N 33/28*    (2006.01)
*G01N 23/223*   (2006.01)

(52) U.S. Cl.
CPC ....... *G01N 23/223* (2013.01); *G01N 33/2888* (2013.01)

(58) Field of Classification Search
CPC ................................ G01N 31/22; G06F 15/00
(Continued)

(56) References Cited

U.S. PATENT DOCUMENTS 6,140,980 A * 10/2000 Spitzer .................. A61B 3/113
                                                    257/E21.614
7,203,283 B1 * 4/2007 Puusaari ................ H01J 35/08
                                                    378/140
(Continued)

FOREIGN PATENT DOCUMENTS

CN    102563328    7/2012
EP    0916940      9/2004
SU    894461       12/1981

OTHER PUBLICATIONS

International Search Report and Written Opinion for corresponding PCT application PCT/GB2014/052552 dated Dec. 3, 2014.
(Continued)

*Primary Examiner* — Don Wong
(74) *Attorney, Agent, or Firm* — Pabst Patent Group LLP

(57) ABSTRACT

The invention relates to lubricant analysis, and to apparatus and methods for carrying out real-time in situ lubricant analysis. The invention extends to apparatus and methods which can measure tribological wear in machinery and, in particular, to the in situ measurement of the elemental composition of lubricant and/or debris caught in a filter within a lubricant-wetted machine.

18 Claims, 3 Drawing Sheets

(58) Field of Classification Search
USPC .................................. 702/27; 378/45, 46
See application file for complete search history.

(56) References Cited

U.S. PATENT DOCUMENTS

| | | |
|---|---|---|
| 2003/0128805 A1 | 7/2003 | Shepard |
| 2004/0213373 A1 | 10/2004 | Wilson |
| 2011/0170659 A1 | 7/2011 | Ohzu |
| 2012/0062894 A1 | 3/2012 | Micali |
| 2013/0191046 A1 | 7/2013 | Henning |
| 2014/0121994 A1* | 5/2014 | Jean .................. G01N 33/2858 702/27 |

OTHER PUBLICATIONS

United Kingdom Search Report for application GB1315024.8 dated Feb. 17, 2014.

* cited by examiner

LUBRICANT ANALYSIS USING X-RAY FLUORESCENCE

CROSS REFERENCE TO RELATED APPLICATIONS

This application is a U.S. national phase filing under 35 U.S.C. § 371 of Intl. Appl. No. PCT/GB2014/052552, filed on Aug. 20, 2014, which claims priority to GB1315024.8, filed on Aug. 22, 2013, which are hereby incorporated herein in their entireties for all purposes.

The invention relates to lubricant analysis, and in particular to apparatus and methods for carrying out real-time in situ lubricant analysis. The invention extends to apparatus and methods which can measure tribological wear in machinery and, in particular, to the in situ measurement of the elemental composition of lubricant and/or debris caught in a filter within a lubricant-wetted machine. The invention also relates to uses of the apparatus and methods for detecting tribological wear in lubricant-wetted machinery.

Monitoring of lubrication oil condition and mechanical tribological wear is considered important by the owners and operators of high value oil-wetted machinery because regular, accurate monitoring can be used to ensure optimum operation, predict impending equipment failure and target maintenance. Equipment owners and operators are keen to ensure that their machinery functions optimally because the consequences of malfunction can be stark. For example, failure of critical systems through tribological wear can result in death (e.g. as a result of aircraft systems failures) and/or financial loss (e.g. as a result of failure or degradation of mining/excavation equipment). Non-optimum operation can also cause reduced machinery lifetime and premature component failure, environmental damage and reduced efficiency. Therefore, ensuring efficient operation of lubricant-wetted machinery is of extreme importance.

Currently, monitoring lubricants for their elemental composition (and thus condition of the lubricant and the lubricated machine) and for the products of tribological wear is carried out by either regular extraction of samples of the lubricant from the machinery, which are then sent to laboratories for assessment (often by flame analysis), or by the removal of the oil filter which is then sent to a laboratory for a complex process of analysis (e.g. X-ray Fluorescence, XRF). These lengthy processes may result in a loss of operating time as well as the loss of the lubricant oil itself. Samples sent to external laboratories may need days or even months before the results are returned. These methods also create waste streams with environmental impact.

There is therefore a need for improved apparatus and methods for determining the elemental composition of lubricant, lubricant systems and/or monitoring tribological wear in lubricant-wetted machinery.

In a first aspect of the invention, there is provided apparatus for the in situ determination of the elemental composition of lubricant and/or debris caught in a filter within a lubricant-wetted machine, the apparatus comprising:

means for exposing a lubricant filter in situ in a lubricant-wetted machine or debris caught in the filter to high energy rays, detection means configured to detect fluorescence emitted by the lubricant filter or the debris, and processing means configured to determine the elemental composition of the lubricant and/or the debris based on the detected fluorescence.

In a second aspect of the invention there is provided a method for determining in situ the elemental composition of lubricant and/or debris caught in a filter within a lubricant-wetted machine, the method comprising:

(i) exposing a lubricant filter in situ in a lubricant-wetted machine or debris caught in the filter to high energy rays;

(ii) detecting fluorescence emitted by the lubricant filter or debris caught in the filter; and (iii) determining the elemental composition of the lubricant and/or the debris based on the detected fluorescence.

Advantageously, by measuring the elemental composition of the lubricant and/or debris in situ within the lubricant filter using the apparatus of the first aspect or the method of the second aspect, it is possible to acquire real-time information about the condition and running efficiency of the lubricant-wetted machine. The apparatus is also able to reliably function at high temperatures in situ, for example in an engine environment. Consequently, the apparatus and method of the invention significantly reduce machine operating costs and increase safety by ensuring optimum function is maintained. Furthermore, the inventors have found that by measuring the elemental composition of lubricant and/or debris caught within the filter of a lubricant-wetted machine using the method of the second aspect or the apparatus of the first aspect, it is possible to detect indications of tribological wear in situ, which may not be detected by current in situ oil analysis systems.

Therefore, preferably the apparatus and method are configured to detect tribological wear within (a) the lubricant-wetted machine and/or (b) the lubricant itself and/or (c) debris in the lubricant and/or (d) debris caught in a filter within the machine.

Thus, in a third aspect there is provided apparatus for the in situ detection of tribological wear of a lubricant-wetted machine, the apparatus comprising:— means for exposing a lubricant filter in situ in a lubricant-wetted machine or debris caught in the filter to high energy rays, detection means configured to detect fluorescence emitted by the lubricant filter, the lubricant, debris caught in the lubricant and/or the debris caught in a filter within the machine, and processing means configured to determine the presence of tribological wear of the machine based on the detected fluorescence.

In a fourth aspect of the invention there is provided a method for detecting in situ tribological wear of a lubricant-wetted machine, the method comprising:

(i) exposing a lubricant filter in situ in a lubricant-wetted machine or debris caught in the filter to high energy rays;

(ii) detecting fluorescence emitted by the lubricant filter, the lubricant, debris caught in the lubricant and/or the debris caught in a filter within the machine; and (iii) detecting for the presence of tribological wear of the machine based on the detected fluorescence.

In a fifth aspect, there is provided a lubricant-wetted machine comprising, or fitted with, the apparatus according to the first aspect or third aspect.

The use of high temperature detectors and associated electronics in a suitable configuration allows measurements to be made in situ.

The lubricant-wetted machine may be any machine or apparatus which requires the use of lubricant or oil, such as an engine, heavy plant machinery, railway locomotives, road or automotive vehicles, ships, aircrafts, transformers, etc.

It will be appreciated that a lubricant may be any substance that is capable of protecting a lubricant-wetted machine against wear, reducing friction between moving surfaces or preventing rust and/or corrosion. A lubricant can also carry contaminants away from their site of production. The type of lubricants used in machinery usually depends on the sector and machinery under test. The lubricant may comprise a base oil, such as a petroleum fraction or a synthetic oil, such as a polyolefin, an ester, a silicone or a fluorocarbon. Standard motor oils, such as single, multi-grade types, synthetic or bio-based oils may be tested, as would aerospace oils, such as tribolube synthetic lubricants. Lubricants used in wind turbines and helicopters may also be tested. The apparatus may be used to test debris build-up in the grease used in bearings etc. As such, the apparatus of the invention has wide application in aviation machinery.

The apparatus and method of the invention may be used to detect debris particles having an average diameter of less than 0.5 mm, and preferably less than 0.05 mm. As described in the examples, debris particles of less than 25-50 µm are detectable. The means for exposing the lubricant filter or filter debris to the high energy rays is preferably configured to emit X-rays, electrons or gamma rays. It is preferred however that the high energy rays are X-rays. The high energy rays may be in the range of 0.1-50 keV, preferably 0.1-35 keV.

The source of high energy rays may comprise a cold cathode source, an electron bombardment source, or a graphene or radioisotope source, dependent on the application.

The detection means may comprise a spectroscopic photon-counting sensor, or an X-ray fluorescence detector. Preferably, however, the detection means comprises an X-ray fluorescence detector. The detection means is preferably capable of detecting photons having energy within the range of 0.1-50 keV, preferably within the range of 0.1-35 keV. The detection means preferably has an energy resolution of <1 keV across the whole energy range.

Advantageously, and preferably, the apparatus according to the invention is capable of operating at high temperatures (e.g. 100° C. and even greater). The use of detectors and associated electronics (based on wide band gap semiconductor materials) will allow measurements at elevated temperatures. The detection means may be based on one of a number of materials, e.g. AlGaAs, GaAs, Si, SiC, CdZnTe and CdTe. Preferably, the detection means is based on silicon (Si).

There is an increasing demand for radiation detectors that can operate in extremely harsh environments, such as in space and the automotive, aeronautic and nuclear industries. For example, planetary exploration places high demands on instrumentation, including extreme thermal operating conditions, low mass, stringent power constraints and high radiation tolerance. Semiconductor materials in general allow the fabrication of detectors that offer direct spectroscopic detection of fluorescence from elements (material).

Advantageously, therefore, wide band gap semiconductors can operate at elevated temperatures while still offering spectroscopic detection. For example, the material $Al_xGa_{1-x}As$ is widely used in GaAs-based electronic and optoelectronic devices. Any composition of $Al_xGa_{1-x}As$ can be grown lattice-matched to the GaAs substrates, which are commercially available in diameters of 150 mm. As a result, using current epitaxial wafer growth technologies, high quality $Al_xGa_{1-x}As$ material of reasonable thickness (e.g. several microns) are achievable with negligible growth defects. With high quality material growth and large band gaps of high Al-content $Al_xGa_{1-x}As$, e.g. 2.09 eV for $Al_{0.8}Ga_{0.2}As$], $Al_xGa_{1-x}As$ diodes tend to exhibit low intrinsic reverse leakage current at room temperature without any device passivation. Large band gap $Al_xGa_{1-x}As$ may thus be preferred for X-ray detection at room temperature and above.

The processing means is preferably a computer, which is configured to analyse and interpret the detected fluorescence data. Preferably, the processing means is configured to convert the detected fluorescence signal emitted by the lubricant and/or debris within the lubricant and/or lubricant filter and/or debris caught in/on the filter into a spectrum, wherein different peaks in the spectrum correspond to the existence and relative quantity of different chemical elements within the lubricant or filter or debris in the filter or lubricant of the lubricant-wetted machine. Thus, the processing means is configured to compare the spectrum of a lubricant filter analysed at two different points in time, and thereby determine real-time information about the elemental composition of the lubricant, debris in the lubricant and debris with the filter within the lubricant-wetted machine.

Accordingly, the method of the second or fourth aspect preferably comprises converting the detected fluorescence signal emitted by the lubricant and/or debris within the lubricant and/or lubricant filter and/or debris caught in/on the filter into a spectrum, wherein different peaks in the spectrum correspond to the existence and relative quantity of different chemical elements within the lubricant or filter or debris in the filter or lubricant of the lubricant-wetted machine. Thus, the method comprise comparing the spectrum of a lubricant filter analysed at two different points in time, and thereby determining real-time information about the elemental composition of the lubricant, debris in the lubricant and debris with the filter within the lubricant-wetted machine.

Any element may be detected within the lubricant or debris, and may be compared between the two time points. Preferably, but not exclusively, the chemical elements detected within the lubricant or debris, and which may be compared between the two time points, are selected from the group consisting of: Fe (Iron), Cu (Copper), Zn (Zinc), Mo (Molybdenum), Al (Aluminium), Ni (Nickel), Cr (Chromium) and Pb (Lead). An increase or decrease, depending on the elements being assessed and their role in the lubricant or machinery, over time is indicative of tribological wear.

In one embodiment, the apparatus is preferably configured to generate an alert signal when the elemental composition of the lubricant reaches user (e.g. machine's operator or manufacture) definable levels.

In one embodiment, the apparatus is preferably configured to generate an alert signal when the lubricant or lubricant-wetted machine suffers, or is predicted to be about to suffer, tribological wear, or impending failure.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying Figures, in which:—

EXAMPLES

The detection of machinery wear and/or component failure is an important aspect of running any machine. In addition, deciding when to change the lubricant in a vehicle is difficult and is critical to optimum and economical operation. If one were to bring in their vehicle too early for an oil change, it would result in a waste of money on fresh lubricant when it is unnecessary and the vehicle would be off the road unnecessarily. Conversely, bringing the vehicle in too late means that more money may be spent on fuel as it may not be running efficiently, and the vehicle may not be protected possibly resulting in higher maintenance costs. The inventors have therefore developed an apparatus and method of continuously monitoring in situ the elemental composition of lubricant in a vehicle and debris present on an oil filter.

Example 1

X-Ray Fluorescence Analysis of Used Motor Car Engine Oil Samples

The inventors first confirmed that it was possible to determine the elemental composition of lubricant extracted from a used motor car using X-ray fluorescence (XRF). They also found that the elemental composition of lubricant oil is a strong indicator of tribological wear.

Figure 1:
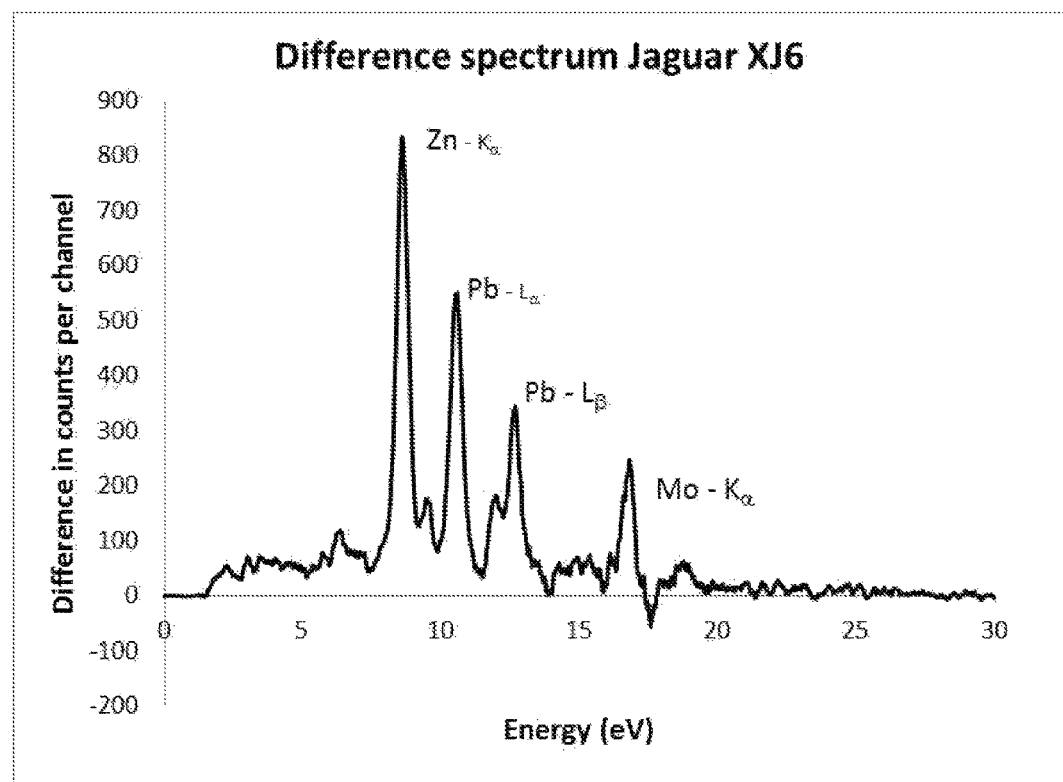
FIG. 1 shows an X-ray fluorescence difference spectra obtained from subtracting the spectra from new oil and oil that has been used in a Jaguar XJ6 engine.

Early X-Ray fluorescence measurements of liquid samples of motor car engine oil (used and clean) showed positive data. Samples from a Jaguar XJ6 engine resulted in a clearly detectable difference between used and clean oils, as shown in FIG. 1. As can be seen, there is a clear change in the amount of zinc (Zn), lead (Pb) and molybdenum (Mo) in the used oil compared to unused oil, as reflected by the four distinct peaks.

Example 2

X-Ray Fluorescence Analysis of Used Motor Car Engine Oil Samples

Following the promising results described in Example 1, the inventors then turned their attention to the analysis of oil filters per se, and in particular debris found on filters, to increase measurement sensitivity. By analysing the filters with X-ray fluorescence spectroscopy the debris associated with tribological wear is detected at the element level and from this the condition of the system can be inferred. The inventors have obtained consistent and encouraging results.

Figure 2:
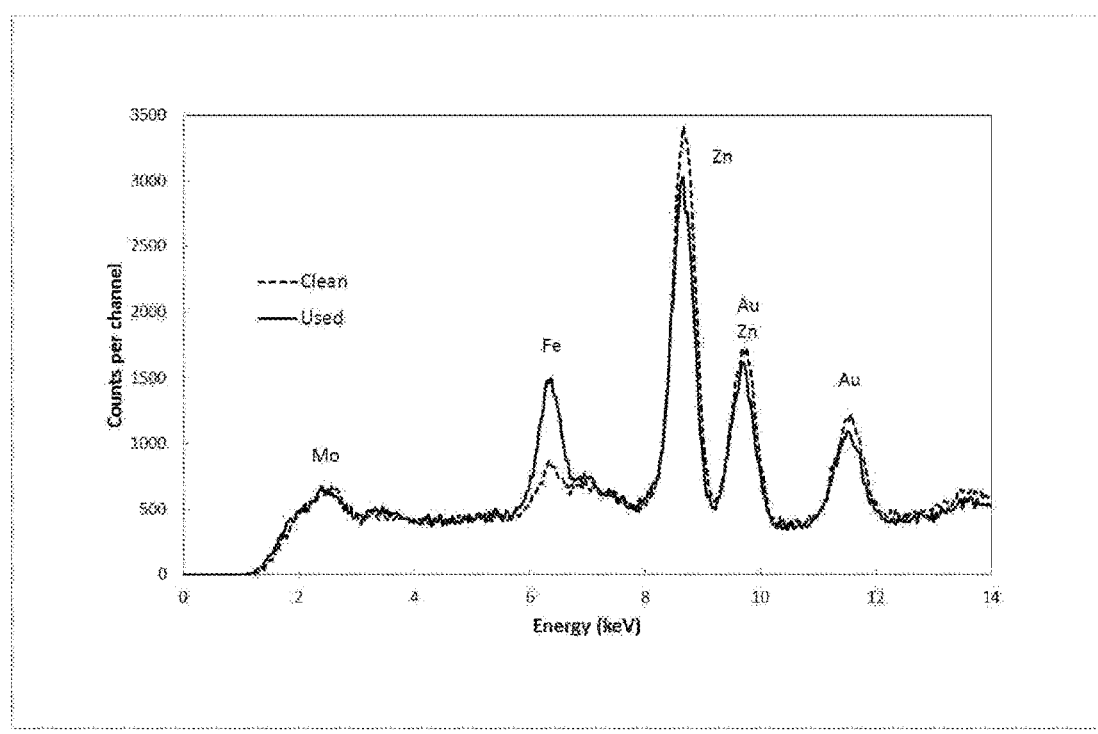
FIG. 2 is a comparison of X-ray fluorescence spectra of a used oil filter showing signs of lubricant and engine wear, and a clean, reference oil filter.

Referring to FIG. 2, there is shown X-ray fluorescence data taken from a representative automotive oil filter which displayed a large increase in Fe (iron) particles in the used filter, indicating that there is significant tribological wear in the machinery of this vehicle. The inventors have also performed scanning electron microscopy (SEM) on the used filter, and these data clearly shows iron particles having diameters in the range of ~25-50 µm. This is highly advantageous because existing x-ray fluorescence systems are unable to detect particles below 0.5 mm in size. To some extent, this may be acceptable for gearboxes, where debris particles tend to be larger, but an engine oil monitor would need to detect smaller particles.

The inventors have therefore been able to unambiguously detect tribological wear products in the used samples by analysing and comparing the oil in clean and used filters. Zinc (Zn) is used as a friction-reducing oil additive, and shows decreased levels in the used oil sample. This indicates that the lubricant itself is also degraded and in need of replacement. The two gold (Au) peaks are from a component of the prototype detector Example 3

In Situ Lubricant Analysis Apparatus

Figure 3:
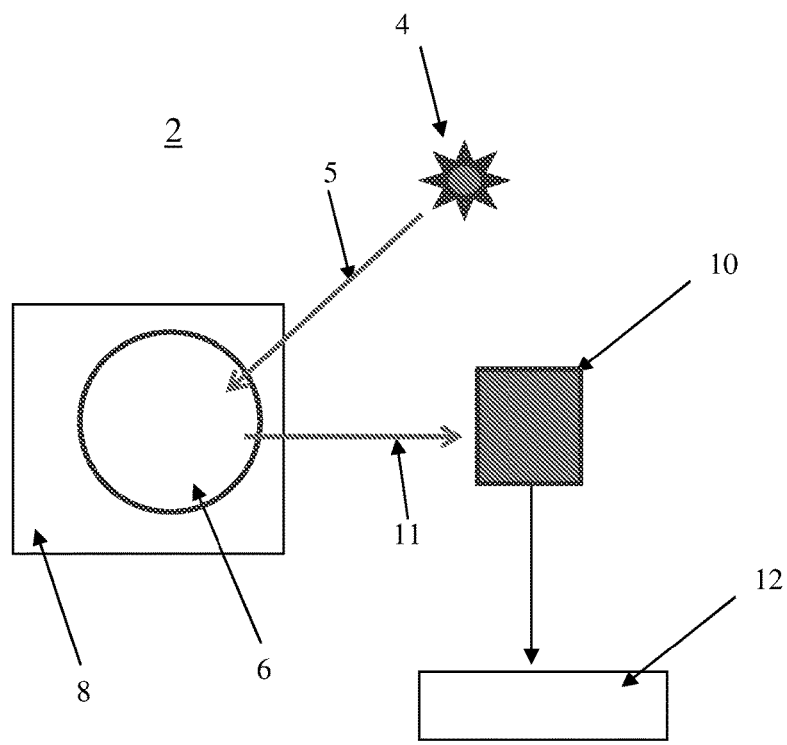
FIG. 3 is a schematic view of one embodiment of a lubricant analysis apparatus of the invention. The exact geometry of the system will vary dependent on the application and layout of other components.

Following on from the data generated in Examples 1 and 2, the inventors developed an in situ lubricant analysis apparatus 2, as shown in FIG. 3, for attachment to a lubricant-wetted machine 8, e.g. an engine. The apparatus 2 includes an X-ray source 4, which emits X-rays 5 towards a filter 6 disposed in situ within the lubricant-wetted machine 8. X-ray fluorescence (XRF) n emitted by the residue (debris) on the filter 6 or lubricant debris thereon is detected by an X-ray detector 10.

The apparatus 2 includes a processor 12, which determines the elemental composition of the lubricant or debris present on the filter 6 based on the information provided by the detected X-ray fluorescence 11. The processor 12 is configured to analyse and interpret the detected fluorescence data 11 of the high energy rays 11 emitted by the lubricant filter or filter debris by converting it into a spectrum, for example as shown in FIG. 2. Different peaks in the spectrum correspond to different chemical elements and their abundance within the lubricant filter of the lubricant-wetted machine 8 (e.g. Fe (Iron), Cu (Copper), Zn (Zinc), Mo (Molybdenum), Pb (Lead)). The processor includes memory which is pre-programmed with "normal" levels of each of these elements, and above (or below depending on element and its role) which changes can be an indication of tribological wear.

Thus, by comparing the spectrum of a lubricant filter 6 analysed at two different points in time (depending on the machine, lubricant, xray detector/emitter and operating conditions) and/or against the pre-programmed "normal" levels of each element, the apparatus 2 determines real-time information about the elemental composition of the lubricant within the lubricant-wetted machine 8. This comparison is also used to determine the rate and/or amount of tribological wear that has occurred in the lubricant-wetted machine 8. The processor 12 is loaded with software which is arranged to generate an alarm signal when the elemental composition of the lubricant is such that the abundance of certain elements in the lubricant or filter residue deviates from the pre-programmed "normal" level.

Example 4

X-Ray Fluorescence Analysis

Figure 4:
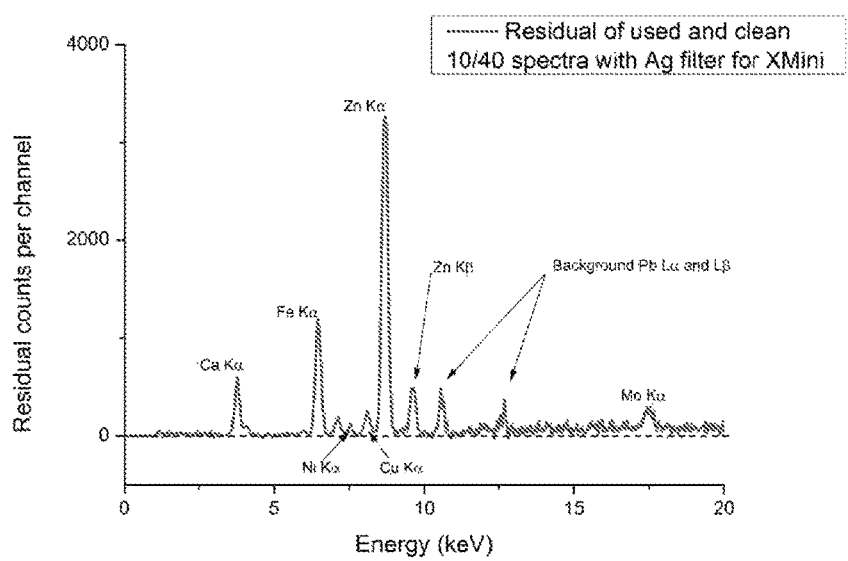
FIG. 4 shows a residual X-ray fluorescence spectrum (subtraction of clean spectrum from used spectrum) of 10/40 Ag filter using a Silicon detector.

Oil filter samples from VFR Motor Services were analysed using a new X-ray/detector combination, involving a silicon detector. By analysing the filters with X-ray fluorescence, the inventors have produced much more consistent results, as shown in FIG. 4, which illustrates the residuals from one oil filter experiment and indicates the presence of a number of elements, including Fe, Ni and Cu, which could not be measured previously.

SUMMARY

Advantages of the apparatus 2 reside in the fact that it can be used to detect early indications of tribological wear in situ (which are not detected by current in situ oil analysis systems) by measuring the elemental composition of lubricant or the debris/residue within the filter 6 of a lubricant-wetted machine 8. In addition, by measuring the elemental composition of the lubricant or residue in situ within the lubricant filter 6, it is possible to acquire real-time information about the condition and running efficiency of the lubricant-wetted machine 8. Consequently, the apparatus 2 significantly reduces machine operating costs and increases safety by ensuring optimum function is maintained. The real-time analysis of the lubricant composition in situ provides a real-time read-out of key oil contaminants. The measurements from the apparatus would ensure that the oil is changed when it needs to be, and not before. The measurements would ensure preventative and reparative maintenance is appropriately targeted.

The invention claimed is:

1. Apparatus for the in situ determination of the elemental composition of lubricant and/or debris caught in a filter within a lubricant-wetted machine, the apparatus comprising:
   a high energy ray source configured to expose a lubricant filter in situ in a lubricant-wetted machine or debris caught in the filter to high energy rays,
   a detector comprising a wide band gap semiconductor material and comprising a spectroscopic photon-counting sensor which is configured to detect fluorescence emitted by the lubricant filter or the debris, and
   a processor configured to determine the elemental composition of the lubricant and/or the debris based on the detected fluorescence.

2. Apparatus according to claim 1, wherein the apparatus is configured to detect tribological wear within (a) the lubricant-wetted machine and/or (b) the lubricant itself and/or (c) debris in the lubricant and/or (d) debris caught in a filter within the machine.

3. Apparatus according to claim 1, wherein the high energy ray source configured to expose the lubricant filter or filter debris to the high energy rays is configured to emit X-rays, electrons or gamma rays.

4. Apparatus according to claim 1, wherein the high energy ray source is a cold cathode source, an electron bombardment source, or a graphene or radioisotope source.

5. Apparatus according to claim 1, wherein the detector is based on a material selected from AlGaAs, GaAs, SiC, CdZnTe and CdTe.

6. Apparatus according to claim 1, wherein the detector is based on the material $Al_xGa_{1-x}As$.

7. Apparatus according to claim 1, wherein the processor is configured to convert the detected fluorescence signal emitted by the lubricant and/or debris within the lubricant and/or lubricant filter and/or debris caught in/on the filter into a spectrum, wherein different peaks in the spectrum correspond to the existence and relative quantity of different chemical elements within the lubricant or filter or debris in the filter or lubricant of the lubricant-wetted machine.

8. Apparatus according to claim 1, wherein the processor is configured to compare the spectrum of a lubricant filter analyzed at two different points in time, and thereby determine real-time information about the elemental composition of the lubricant, debris in the lubricant and debris with the filter within the lubricant-wetted machine.

9. Apparatus according to claim 8, wherein the comparison is used to determine the rate and/or amount and/or location and/or origin of tribological wear that has occurred in the lubricant or lubricant-wetted machine.

10. Apparatus according to claim 8, wherein the chemical elements detected within the lubricant or debris, and which are compared between the two time points, are selected from the group consisting of: Fe (Iron), Cu (Copper), Zn (Zinc), Mo (Molybdenum), Al (Aluminium), Ni (Nickel), Cr (Chromium) and Pb (Lead).

11. Apparatus according to claim 1, wherein the apparatus is configured to generate an alert signal when the elemental composition of the lubricant reaches user definable levels, or wherein the apparatus is configured to generate an alert signal when the lubricant or lubricant-wetted machine suffers, or is predicted to be about to suffer, tribological wear, or impending failure.

12. Apparatus according to claim 1, wherein the lubricant is selected from a group consisting of a standard motor oil, synthetic or bio-based oil; and aerospace oils.

13. A lubricant-wetted machine comprising, or fitted with, an apparatus comprising:
   a high energy ray source configured to expose a lubricant filter in situ in a lubricant-wetted machine or debris caught in the filter to high energy rays,
   a detector comprising a wide band gap semiconductor material and comprising a spectroscopic photon-counting sensor which is configured to detect fluorescence emitted by the lubricant filter or the debris, and
   a processor configured to determine the elemental composition of the lubricant and/or the debris based on the detected fluorescence.

14. A method for determining in situ the elemental composition of lubricant and/or debris caught in a filter within a lubricant-wetted machine, the method comprising:
   (i) exposing a lubricant filter in situ in a lubricant-wetted machine or debris caught in the filter to high energy rays;
   (ii) detecting fluorescence emitted by the lubricant filter or debris caught in the filter using a detector comprising a wide band gap semiconductor material and comprising a spectroscopic photon-counting sensor; and
   (iii) determining the elemental composition of the lubricant and/or the debris based on the detected fluorescence.

15. A method according to claim 14, wherein the method comprises converting the detected fluorescence signal emitted by the lubricant and/or debris within the lubricant and/or lubricant filter and/or debris caught in/on the filter into a spectrum, wherein different peaks in the spectrum correspond to the existence and relative quantity of different chemical elements within the lubricant or filter or debris in the filter or lubricant of the lubricant-wetted machine.

16. A method according to claim 14, wherein the method comprises comparing the spectrum of a lubricant filter analyzed at two different points in time, and thereby determining real-time information about the elemental composition of the lubricant, debris in the lubricant and debris with the filter within the lubricant-wetted machine.

17. Apparatus for the in situ detection of tribological wear of a lubricant-wetted machine, the apparatus comprising:

a high energy ray source configured to expose a lubricant filter in situ in a lubricant-wetted machine or debris caught in the filter to high energy rays, a detector comprising a wide band gap semiconductor material and comprising a spectroscopic photon-counting sensor which is configured to detect fluorescence emitted by the lubricant filter, the lubricant, debris caught in the lubricant and/or the debris caught in a filter within the machine, and a processor configured to determine the presence of tribological wear of the machine based on the detected fluorescence.

18. A method for detecting in situ tribological wear of a lubricant-wetted machine, the method comprising:
(i) exposing a lubricant filter in situ in a lubricant-wetted machine or debris caught in the filter to high energy rays;
(ii) detecting fluorescence emitted by the lubricant filter, the lubricant, debris caught in the lubricant and/or the debris caught in a filter within the machine using a detector comprising a wide band gap semiconductor material and comprising a spectroscopic photon-counting sensor; and
(iii) detecting for the presence of tribological wear of the machine based on the detected fluorescence.

* * * * *